(12) United States Patent
Liu et al.

(10) Patent No.: US 9,857,323 B2
(45) Date of Patent: Jan. 2, 2018

(54) METHOD FOR MEASURING AMOUNTS OF COMPONENTS AND CALORIFIC VALUE OF COAL GAS

(71) Applicant: Wuhan Cubic Optoelectronics Co., Ltd., Wuhan (CN)

(72) Inventors: Zhiqiang Liu, Wuhan (CN); Youhui Xiong, Wuhan (CN); Tao He, Wuhan (CN); Pingjing Shi, Wuhan (CN)

(73) Assignee: Wuhan Cubic Optoelectronics Co., Ltd., Wuhan (CN)

( * ) Notice: Subject to any disclaimer, the term of this patent is extended or adjusted under 35 U.S.C. 154(b) by 548 days.

(21) Appl. No.: 14/289,622

(22) Filed: May 28, 2014

(65) Prior Publication Data

US 2014/0262836 A1 Sep. 18, 2014

Related U.S. Application Data

(63) Continuation-in-part of application No. PCT/CN2012/080795, filed on Aug. 30, 2012.

(30) Foreign Application Priority Data

Dec. 22, 2011 (CN) .......................... 2011 1 0435862

(51) Int. Cl.
*G01N 27/26* (2006.01)
*G01N 21/3504* (2014.01)
*G01N 33/22* (2006.01)
*G01N 7/18* (2006.01)

(52) U.S. Cl.
CPC ............... *G01N 27/26* (2013.01); *G01N 7/18* (2013.01); *G01N 21/3504* (2013.01); *G01N 33/225* (2013.01)

(58) Field of Classification Search
CPC ......... G01N 27/26; G01N 7/18; G01N 33/225
See application file for complete search history.

(56) References Cited

U.S. PATENT DOCUMENTS

2004/0227087 A1* 11/2004 Markham .......... G01N 21/3504
250/339.08

FOREIGN PATENT DOCUMENTS

| DE | 102005005727 A1 * | 8/2006 | ......... G01N 21/3504 |
| DE | 102008038278 B3 * | 10/2009 | ......... G01N 21/3504 |
| DE | 102008029553 B3 * | 11/2009 | ........... G01N 33/225 |

OTHER PUBLICATIONS

European Search Report and Written Opinion for Application EP12860685.*

* cited by examiner

*Primary Examiner* — J. Christopher Ball
(74) *Attorney, Agent, or Firm* — Matthias Scholl, PC; Matthias Scholl

(57) ABSTRACT

A method for measuring the component and calorific value of goal gas. The method includes measuring a volume concentration of $H_2$ ($T_{H2}$) using a thermal conductivity detector (TCD), measuring a volume concentration of $O_2$ using an electrochemical detector (ECD), measuring volume concentrations of CO, $CO_2$, $CH_4$, and $C_nH_m$ in the coal gas, revising an interference of $CH_4$ in $C_nH_m$, revising a measured volume concentration of $H_2$, and calculating the calorific value of the coal gas.

10 Claims, 4 Drawing Sheets

METHOD FOR MEASURING AMOUNTS OF COMPONENTS AND CALORIFIC VALUE OF COAL GAS

CROSS-REFERENCE TO RELATED APPLICATIONS

This application is a continuation-in-part of International Patent Application No. PCT/CN2012/080795 with an international filing date of Aug. 30, 2012, designating the United States, now pending, and further claims priority benefits to Chinese Patent Application No. 201110435862.3 filed Dec. 22, 2011. The contents of all of the aforementioned applications, including any intervening amendments thereto, are incorporated herein by reference.

BACKGROUND OF THE INVENTION

Field of the Invention

The invention relates to a method for measuring the components and calorific value of coal gas.

Description of the Related Art

As a typical manual chemical analyzer, Orsat gas analyzer is characterized by low price, convenient operation and easy maintenance. However, the manual operation has low accuracy and low speed, and cannot meet the needs of industrial development. In recent years, the chromatograph has been promoted widely, but the gas to be tested must be separated using a plurality of chromatographic columns in the presence of a carrier gas, which causes the difficulty in the real-time online test.

Infrared gas analyzers have been used for years, but the technology can only analyze one or two components. In addition, gas analyzers suffer from high price and complex maintenance, and cannot accurately measure the amount of $CH_4$ in the coal gas due to interference from other hydrocarbons. The volume concentration of $H_2$ and $O_2$ in the coal gas cannot be measured using a nondispersive infrared (NDIR) method. The volume concentration of $H_2$ is usually measured with a thermal conductivity detector (TCD), and that of $O_2$ is measured with an electrochemical detector (ECD). $CH_4$ and other $C_nH_m$ in the coal gas interfere with each other, and $CH_4$ and $CO_2$ interfere with $H_2$.

Due to the significant mutual interference of $C_nH_m$ and $CH_4$, it is very difficult to accurately measure various components in the coal gas, especially $CH_4$, $C_nH_m$, CO and $H_2$ which provide the main source of calorific value. Therefore, it is necessary to develop a method to accurately measure a variety of components in the coal gas, calculate the calorific value of coal gas, and effectively eliminate the interference between gases.

SUMMARY OF THE INVENTION

In view of the above-described problems, it is one objective of the invention to provide a method for more accurately measuring the components and calorific value of coal gas.

To achieve the above objective, in accordance with one embodiment of the invention, there is provided a method for measuring the components and calorific value of coal gas, the method comprising the following steps:

1) measuring a volume concentration of $H_2$ ($T_{H2}$) using a thermal conductivity detector (TCD), measuring a volume concentration of $O_2$ using an electrochemical detector (ECD);

2) measuring volume concentrations of CO, $CO_2$, $CH_4$, and $C_nH_m$ in the coal gas, represented by $T_{CO}$, $T_{CO2}$, $T_{CH4}$, and $T_{CnHm}$, respectively, using a non-dispersive infrared (NDIR) technology;

3) revising an interference of $CH_4$ in $C_nH_m$ using an equation $R_{CnHm} = T_{CnHm} - A \times T_{CH4}$, in which, A represents an undetermined coefficient, and $T_{CnHm}$ and $T_{CH4}$ represent the volume concentrations of $C_nH_m$ and $CH_4$ measured with the NDIR, respectively;

4) revising a measured volume concentration of $H_2$ using the equation $R_{H2} = T_{H2} - a \times (T_{CH4} + R_{CnHm}) - b \times T_{CO2}$, in which, $T_{H2}$ represents the measured volume concentration of $H_2$ using the TCD, $T_{CH4}$ and $T_{CO2}$ represent the volume concentrations of $CH_4$ and $CO_2$ measured using the NDIR, respectively, $R_{CnHm}$ represents a revised volume concentration of $C_nH_m$, and a and b represents undetermined coefficients; and 5) calculating the calorific value of the coal gas using the equation $Q = T_{CO} \times 12.64 + R_{H2} \times 18.79 + T_{CH4} \times 35.88 + R_{CnHm} \times 93.18$, in which, $T_{CO}$ and $T_{CH4}$ represent measured volume concentrations, and $R_{H2}$ and $R_{CnHm}$ represent revised volume concentrations.

In a class of this embodiment, in the process of measuring the volume concentration of $CH_4$ using the NDIR, a center wavelength (CWL)/half-peak bandwidth (HWBP) of a selected narrowband filter is $7.85 \pm 0.05$ μm/$180 \pm 5$ nm.

In a class of this embodiment, in the process of measuring the volume concentration of $C_nH_m$ using the NDIR, a CWL/HWBP of a selected narrowband filter is $3.46 \pm 0.05$ μm/$120 \pm 5$ nm.

In a class of this embodiment, in the process of measuring the volume concentration of CO using the NDIR, a CWL/HWBP of a selected narrowband filter is $4.66 \pm 0.05$ μm/$90 \pm 5$ nm.

In a class of this embodiment, in the process of measuring the volume concentration of $CO_2$ using the NDIR, a CWL/HWBP of a selected narrowband filter is $4.26 \pm 0.05$ μm/$120 \pm 5$ nm.

Compared with the existing test methods, the method according to embodiments of the invention has the following advantages: the invention can simultaneously measure a variety of gas components, reduce the interference between different gases by optimizing NDIR narrowband filter parameters, measure $C_nH_m$ with the filter of 3.46 μm wavelength, convert other hydrocarbons into $C_3H_8$, and facilitate calculating the calorific value of coal gas according to the obtained volume concentration of gas. The manufacturing cost of the analytical instrument in this method is ⅓ as much as that of the calorimeter in the traditional combustion method, and only 1/10 as much as that of the mass spectrum analyzer. Its analysis speed is 30 times more than that of the conventional chromatograph.

DETAILED DESCRIPTION OF THE EMBODIMENTS

For further illustrating the invention, experiments detailing a method for measuring the components and calorific value of coal gas are described hereinbelow combined with examples.

Example 1 Gas Analysis of Coal Gas from Biomass Gasification Using Six-Component Gas Analyzer 1. Selection of Various Gas Filter Parameters, Gas Chamber Length, and Measuring Range of Gas Detectors.

Figure 1:
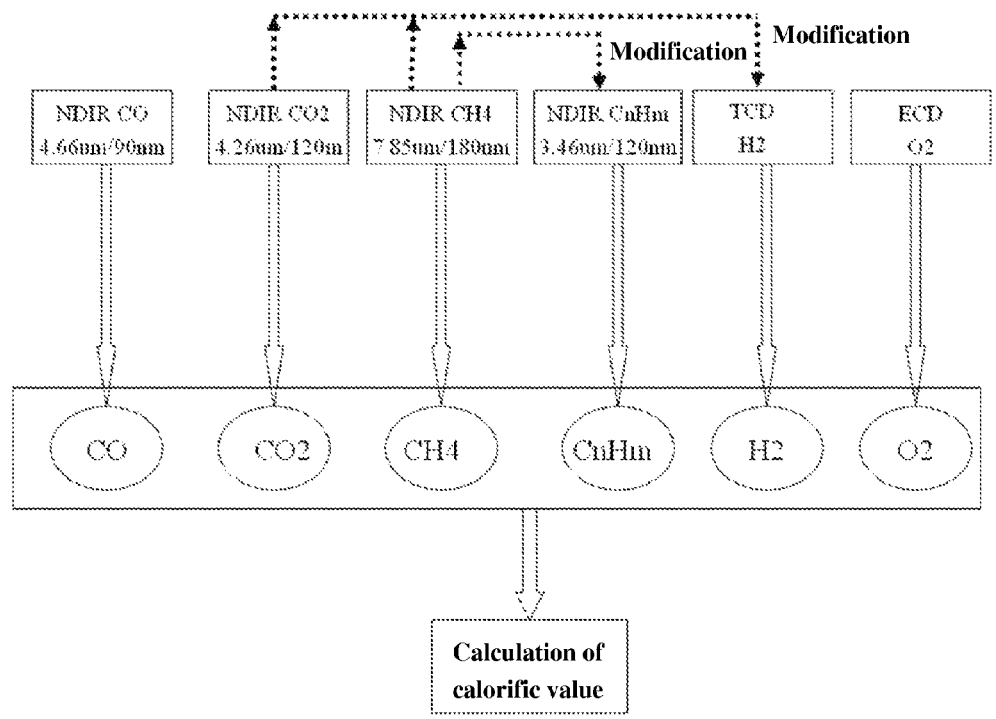
FIG. 1 is a principle diagram for analysis of components and calorific value of coal gas in accordance with one embodiment of the invention.
Figure 2:
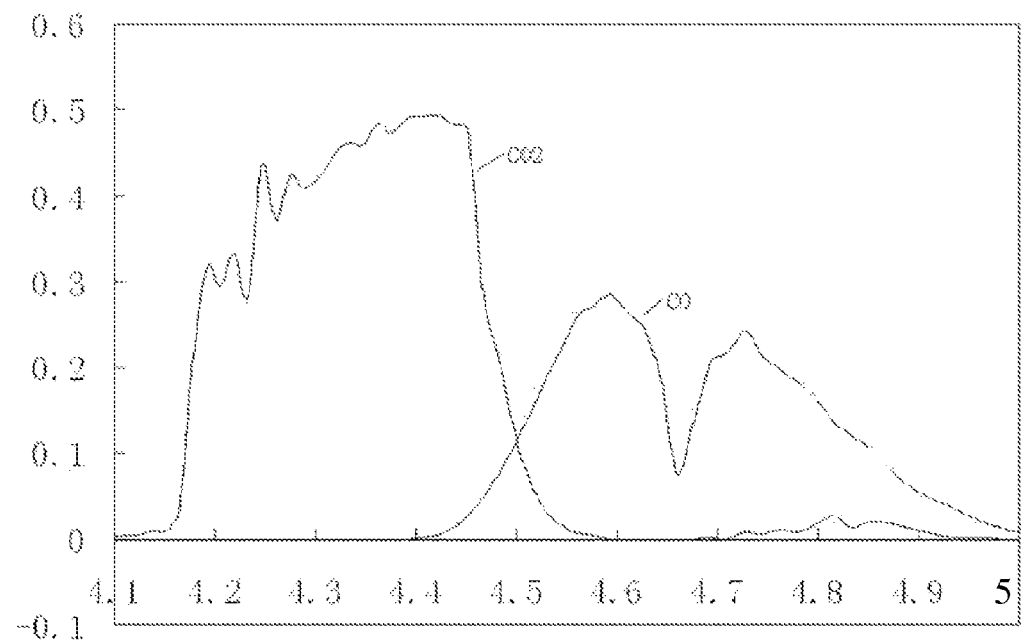
FIG. 2 is an infrared absorption spectrum of CO, $CO_2$ and $CH_4$.

As shown in the infrared absorption spectra of CO and $CO_2$ in FIG. 2, the absorption peak of CO at 4.66 μm is not affected by $CO_2$, and the absorption peak of $CO_2$ at 4.26 μm is not affected by CO. Thus, a CO detector with the measuring range of 40% and a $CO_2$ detector with the measuring range of 30% are made, with the narrowband filter parameters respectively of 4.66 μm/90 nm and 4.26 μm/120 nm, reference channel of 3.91 μm, and chamber length respectively of 43 mm and 2 mm.

Figure 3:
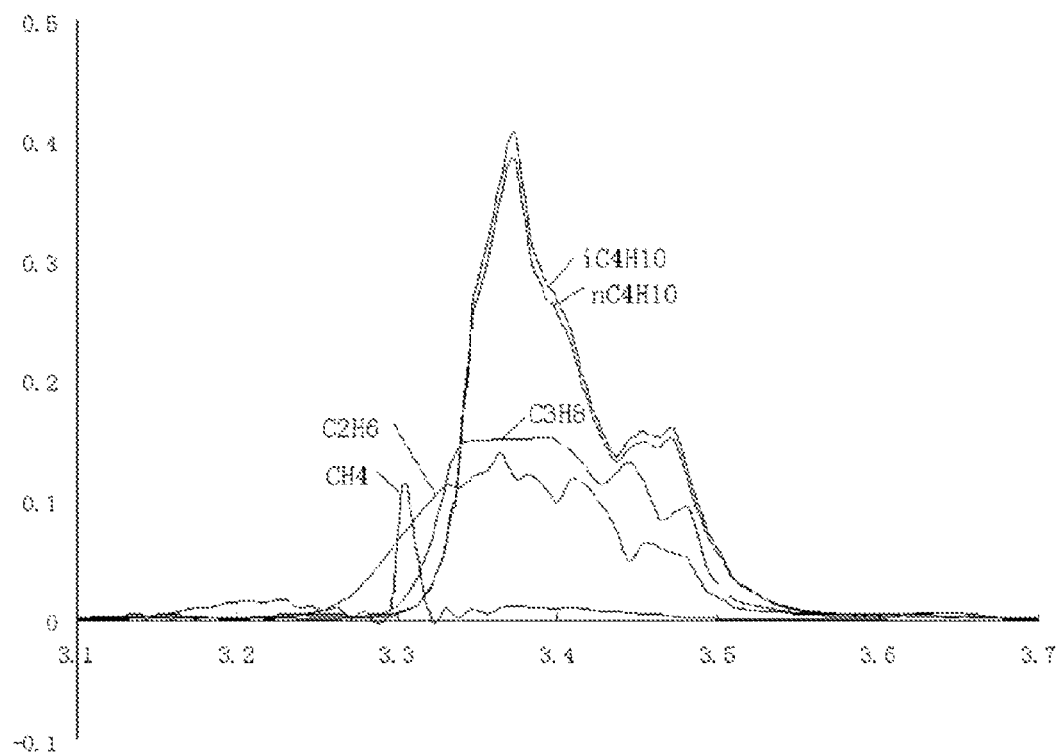
FIG. 3 is a mutual interference pattern of hydrocarbons approximately at 3.3 μm.
Figure 4:
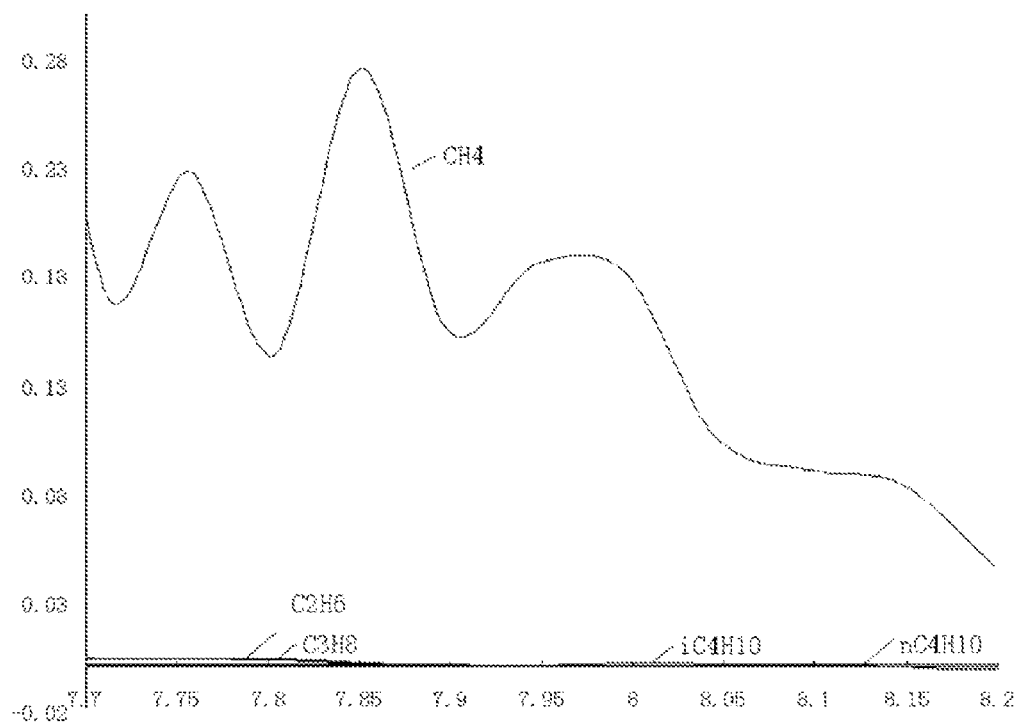
FIG. 4 is an infrared absorption spectrum of $CH_4$.

Then, based on the infrared absorption spectra of $CH_4$, $C_2H_6$, $C_3H_8$ and $C_4H_{10}$ in FIGS. 3-4, the absorption peak at 7.85 μm is selected, instead of the absorption peak at 3.3 μm, in order to eliminate the influence of $C_nH_m$ on $CH_4$ absorption peak. As a result, the $CH_4$ detector with the measuring range of 20% is made, with the narrowband filter parameters of 7.85 μm/180 nm, reference channel of 3.91 μm and $CH_4$ chamber length of 68 mm.

According to the infrared absorption spectrum of $C_nH_m$ in FIG. 3, $C_nH_m$ has absorption peaks at 3.3-3.5 μm. In order to reduce the influence of $CH_4$ on $C_nH_m$, it is necessary to avoid the absorption peak of $CH_4$, and select center wavelength at 3.35-3.5 μm. Test of different filters at 3.35-3.5 μm shows that $C_3H_8$ can represent $C_nH_m$ ($C_nH_m$ is calibrated with $C_3H_8$) with the narrowband filter of 3.46 μm/120 nm as the filter for $C_nH_m$ detector. The $C_nH_m$ detector with the measuring range of 5% is made, with the reference channel of 3.91 μm and $C_nH_m$ chamber length of 43 mm. The test data are provided in Table 1.

TABLE 1

Influence of C1-C5 on the detector at 3.46 μm

| Inlet gas (%) | Volume concentration of $CH_4$ (%) | Volume concentration of $C_nH_m$ (%) | Proportionality coefficient of volume concentration ($C_3H_8/C_nH_m$) | Average proportionality coefficient of volume concentration ($C_3H_8/C_nH_m$) |
|---|---|---|---|---|
| $CH_4$ 0 | 0 | 0 | — | — |
| (C1) 3.79 | 3.76 | 0.11 | — | — |
| 7.68 | 7.71 | 0.22 | — | — |
| 11.67 | 11.66 | 0.34 | — | — |
| 15.78 | 15.80 | 0.45 | — | — |
| 20.00 | 20.01 | 0.57 | — | — |
| $C_2H_6$ 1.01 | 0 | 0.69 | 0.68 | 0.687 |
| (C2) 2.03 | 0 | 1.41 | 0.69 | |
| 3.98 | 0 | 2.73 | 0.69 | |
| $C_3H_8$ 0.43 | 0 | 0.42 | 0.98 | 1.00 |
| (C3) 1.76 | 0.01 | 1.78 | 1.01 | |
| 3.42 | 0.01 | 3.44 | 1.01 | |
| 5.00 | 0.02 | 5.01 | 1.00 | |
| $NC_4$ 1.01 | 0.01 | 1.32 | 1.31 | 1.315 |
| (C4) 2.00 | 0.02 | 2.68 | 1.34 | |
| $IC_4$ 1.01 | 0 | 1.29 | 1.28 | |
| (C4) 1.99 | 0.01 | 2.64 | 1.33 | |
| $NC_5$ 0.998 | 0.01 | 1.67 | 1.67 | 1.68 |
| (C5) | | | | |
| $IC_5$ 1.00 | 0.01 | 1.69 | 1.69 | |
| (C5) | | | | |

TABLE 2

Coefficient of low calorific value of $C_nH_m$

| Gas name | Coefficient of low calorific value (MJ/m³) | Ratio of coefficient of calorific value ($C_nH_m/C_3H_8$) |
|---|---|---|
| $C_2H_6$ | 64.35 | 0.69 |
| $C_3H_8$ | 93.18 | 1.00 |
| $C_4H_{10}$ | 123.16 | 1.32 |
| $C_5H_{12}$ | 156.63 | 1.68 |

From the comparison of Table 1 and Table 2, the proportionality coefficient of the volume concentration of $C_nH_m$ measured with the detector made of the narrowband filter at 3.46 μm/120 nm is very close to its coefficient of calorific value, so the calorific value of $C_nH_m$ can be calculated as that of $C_3H_8$.

Likewise, a TCD of $H_2$ with the measuring range of 20% and an ECD of $O_2$ with the measuring range of 25% are manufactured according to conventional methods.

2. Measurement of the Volume Concentration of Various Gases

CO, $CO_2$, $CH_4$ and $C_nH_m$ are measured using NDIR, and the readings are respectively expressed as $T_{CO}$, $T_{CO2}$, $T_{CH4}$ and $T_{CnHm}$.

The volume concentration of $H_2$ is measured with a TCD, and is expressed as $T_{H2}$.

The volume concentration of $O_2$ is measured with an ECD, and is expressed as $T_{O2}$.

3. Revision of the Gas Volume Concentration and Calculation of the Calorific Value.

1) Revise the Volume Concentration of $C_nH_m$ with $CH_4$.

$CH_4$ has certain influence on $C_nH_m$, so it is also necessary to get the revised volume concentration of $C_nH_m$ ($R_{CnHm}$) through revising the measuring result of $C_nH_m$ ($T_{CnHm}$) obtained from the calibration curve according to the volume concentration of $CH_4$ ($T_{CH4}$).

In order to revise the influence of $CH_4$ on the measuring result of $C_nH_m$, the calibrating gas $CH_4$ is introduced into the six-component gas analyzer present in the biomass gasification system of this example. Volume concentration and measuring result of the calibrating gas are provided in Table 3.

TABLE 3

Volume concentration and measuring result of the calibrating gas $CH_4$

| Volume concentration of the calibrating gas (%) | Measuring result (%) | |
|---|---|---|
| $CH_4$ | $T_{CH4}$ | $T_{CnHm}$ |
| 0 | 0 | 0 |
| 1.88 | 1.90 | 0.05 |
| 3.79 | 3.80 | 0.11 |
| 5.72 | 5.75 | 0.16 |
| 7.68 | 7.70 | 0.22 |
| 9.66 | 9.69 | 0.28 |
| 11.67 | 11.65 | 0.34 |
| 13.71 | 13.70 | 0.40 |
| 15.78 | 15.80 | 0.45 |
| 17.87 | 17.90 | 0.51 |
| 20.00 | 20.02 | 0.57 |

The following correction equation can be obtained through data analysis:

$$R_{CnHm} = T_{CnHm} - A \times T_{CH4}$$

Data in Table 3 are substituted into the equation to conclude that A=0.02868.

Therefore, $$R_{CnHm} = T_{CnHm} - A \times T_{CH4} = T_{CnHm} - 0.02868 \times T_{CH4}$$

2) Revise the Volume Concentration of $H_2$.

The balance gas $N_2$ used to calibrate $H_2$ is greatly different from $CH_4$ and $CO_2$ in the relative thermal conductivity, as shown in Table 4, so $CH_4$ and $CO_2$ have certain influence on the measuring results of $H_2$ using an TCD. $C_nH_m$ is different from $N_2$ in the thermal conductivity, but its content in the coal gas is only about ⅕ as much as $CH_4$, therefore it can be neglected. CO and $O_2$ are very slightly different from $N_2$ in thermal conductivity, and can also be neglected. Hence, it is only necessary to get the revised volume concentration of $H_2$ ($R_{H2}$) through revising the measuring results of $H_2$ ($T_{H2}$) according to the measuring results of $CH_4$ and $CO_2$ ($T_{CO2}$, $T_{CH4}$).

TABLE 4

Thermal conductivity of different gases

| Gas name | Relative thermal conductivity, $\lambda/\lambda_{air}$ | Gas name | Relative thermal conductivity, $\lambda/\lambda_{air}$ |
|---|---|---|---|
| Air | 1.000 | CO | 0.964 |
| $H_2$ | 7.130 | $CO_2$ | 0.614 |
| $O_2$ | 1.015 | $SO_2$ | 0.344 |
| $N_2$ | 0.998 | $NH_3$ | 0.897 |
| He | 5.910 | $CH_4$ | 1.318 |

In order to revise the influence of $CH_4$ and $CO_2$ on the measuring result of $H_2$, the calibrating gases $CH_4$ and $CO_2$ are introduced into the six-component gas analyzer present in the biomass gasification system of this example. Volume concentration and measuring result of the calibrating gases are provided in Table 5:

TABLE 5

Influence of $CH_4$ and $CO_2$ on $H_2$

| Volume concentration of the calibrating gas (%) | | Measuring result (%) | | |
|---|---|---|---|---|
| $CH_4$ | $CO_2$ | $T_{CH4}$ | $T_{CO2}$ | $T_{H2}$ |
| 0 | 0 | 0 | 0 | 0 |
| 0 | 2.75 | 0 | 2.73 | −0.29 |
| 0 | 5.54 | 0 | 5.51 | −0.61 |
| 0 | 8.40 | 0 | 8.36 | −0.93 |
| 0 | 11.30 | 0 | 11.35 | −1.23 |
| 0 | 14.27 | 0 | 14.21 | −1.59 |
| 0 | 17.29 | 0 | 17.34 | −1.90 |
| 0 | 20.37 | 0 | 20.43 | −2.25 |
| 0 | 23.52 | 0 | 23.61 | −2.58 |
| 0 | 26.73 | 0 | 26.69 | −2.96 |
| 0 | 30.00 | 0 | 29.97 | −3.30 |
| 1.88 | 0 | 1.84 | 0 | 0.27 |
| 3.79 | 0 | 3.82 | 0 | 0.54 |
| 5.72 | 0 | 5.76 | 0 | 0.82 |
| 7.68 | 0 | 7.71 | 0 | 1.06 |
| 9.66 | 0 | 9.63 | 0 | 1.38 |
| 11.67 | 0 | 11.62 | 0 | 1.66 |
| 13.71 | 0 | 13.83 | 0 | 1.93 |
| 15.78 | 0 | 15.81 | 0 | 2.23 |
| 17.87 | 0 | 17.91 | 0 | 2.50 |
| 20 | 0 | 19.98 | 0 | 2.80 |

The following correction equation can be obtained through data analysis:

$$R_{H2} = T_{H2} - a \times T_{CH4} - b \times T_{CO2}$$

Data in Table 5 are substituted into the equation to conclude that a=0.13989; b=−0.11026.

Therefore, $$R_{H2} = T_{H2} - a \times T_{CH4} - b \times T_{CO2} = T_{H2} - 0.13989 \times T_{CH4} + 0.11026 \times T_{CO2}.$$

3) Calculate the Calorific Value of Coal Gas

According to the above gas concentration, the calorific value of coal gas is obtained through substituting $T_{CO}$, $T_{CH4}$, $R_{CnHm}$ and $R_{H2}$ into the equation $Q = T_{CO} \times 12.64 + R_{H2} \times 18.79 + T_{CH4} \times 35.88 + R_{CnHm} \times 93.18$; in which, Q is expressed as $MJ/m^3$, 12.64, 18.79, 35.88 and 93.18 are respectively the coefficient of low calorific value of CO, $H_2$, $CH_4$ and $C_nH_m$ expressed as $MJ/m^3$.

This example is provided to design a six-component gas analyzer with the measuring range of CO of 40%, that of $CO_2$ of 30%, that of $CH_4$ of 20%, that of $C_nH_m$ of 5%, that of $H_2$ of 20%, and that of $O_2$ of 25%. This gas analyzer is applicable to many industries, such as air coal gasification, biomass air gasification, blast furnace, and endothermal and exothermal gas generators for heat treatment.

Example 2 Gas Analysis of Coal Gas from Biomass Pyrolysis and Coking Using Six-Component Gas Analyzer 1. Selection of the Length and Measuring Range of Various Gas Chambers Filters in the NDIR gas detector are selected as that in Example 1. Gas chamber design: CO detector with the measuring range of 40% and CO chamber length of 43 mm; $CO_2$ detector with the measuring range of 20% and $CO_2$ chamber length of 3 mm; $CH_4$ detector with the measuring range of 50% and $CH_4$ chamber length of 34 mm; $C_nH_m$ detector with the measuring range of 10% and $C_nH_m$ chamber length of 20 mm.

A $H_2$ detector with the measuring range of 75% and $O_2$ detector with the measuring range of 25% are manufactured according to conventional methods.

2. Measurement of the Volume Concentration of Various Gases

CO, $CO_2$, $CH_4$ and $C_nH_m$ are measured using NDIR, and the readings are respectively expressed as $T_{CO}$, $T_{CO2}$, $T_{CH4}$ and $T_{CnHm}$.

The volume concentration of $H_2$ is measured with a TCD, and is expressed as $T_{H2}$.

The volume concentration of $O_2$ is measured with an ECD, and is expressed as $T_{O2}$.

3. Revision of the Gas Volume Concentration and Calculate the Calorific Value.

1) Revise the Volume Concentration of $C_nH_m$ with $CH_4$.

In order to revise the influence of $CH_4$ on the measuring result of $C_nH_m$, the calibrating gas $CH_4$ is introduced into a six-component gas analyzer present in the biomass pyrolysis and coking system of this example. Volume concentration and measuring result of the calibrating gas are provided in Table 6:

TABLE 6

Volume concentration and measuring result of the calibrating gas $CH_4$

| Standard gas volume concentration (%) | Measuring result (%) | |
| --- | --- | --- |
| $CH_4$ | $T_{CH4}$ | $T_{CnHm}$ |
| 0 | 0 | 0 |
| 4.29 | 4.30 | 0.12 |
| 8.72 | 8.75 | 0.25 |
| 13.3 | 13.28 | 0.38 |
| 18.02 | 18.00 | 0.51 |
| 22.91 | 22.94 | 0.65 |
| 27.96 | 28.00 | 0.78 |
| 33.18 | 33.20 | 0.94 |
| 38.59 | 38.61 | 1.11 |
| 44.19 | 44.23 | 1.26 |
| 50.00 | 50.00 | 1.41 |

The following correction equation can be obtained through data analysis:

$$R_{CnHm}=T_{CnHm}-A\times T_{CH4}$$

Data in Table 6 are substituted into the equation to conclude that A=0.02837.

Therefore, $$R_{CnHm}=T_{CnHm}-A\times T_{CH4}=T_{CnHm}-0.02837\times T_{CH4}$$

2) Revise the Volume Concentration of $H_2$.

In order to revise the influence of $CH_4$ and $CO_2$ on the measuring result of $H_2$, the calibrating gases $CH_4$ and $CO_2$ are introduced into the six-component gas analyzer present in the biomass pyrolysis and coking system of this example. Volume concentration and measuring result of the calibrating gases are provided in Table 7:

TABLE 7

Influence of $CH_4$ and $CO_2$ on $H_2$

| Standard gas volume concentration (%) | | Measuring result (%) | | |
| --- | --- | --- | --- | --- |
| $CH_4$ | $CO_2$ | $T_{CH4}$ | $T_{CO2}$ | $T_{H2}$ |
| 50 | 0 | 0 | 0 | 7.05 |
| 44.19 | 0 | 0 | 1.91 | 6.24 |
| 38.59 | 0 | 0 | 3.81 | 5.44 |

TABLE 7-continued

Influence of $CH_4$ and $CO_2$ on $H_2$

| Standard gas volume concentration (%) | | Measuring result (%) | | |
| --- | --- | --- | --- | --- |
| $CH_4$ | $CO_2$ | $T_{CH4}$ | $T_{CO2}$ | $T_{H2}$ |
| 33.18 | 0 | 0 | 5.71 | 4.68 |
| 27.96 | 0 | 0 | 7.66 | 3.92 |
| 22.91 | 0 | 0 | 9.62 | 3.23 |
| 18.02 | 0 | 0 | 11.61 | 2.55 |
| 13.3 | 0 | 0 | 13.75 | 1.86 |
| 8.72 | 0 | 0 | 15.81 | 1.23 |
| 4.29 | 0 | 0 | 17.91 | 0.61 |
| 0 | 20.00 | 0 | 19.99 | -2.22 |
| 0 | 17.88 | 4.32 | 0 | -1.99 |
| 0 | 15.78 | 8.71 | 0 | -1.74 |
| 0 | 13.72 | 13.28 | 0 | -1.50 |
| 0 | 11.68 | 18.04 | 0 | -1.30 |
| 0 | 9.67 | 22.93 | 0 | -1.05 |
| 0 | 7.69 | 27.92 | 0 | -0.86 |
| 0 | 5.73 | 33.15 | 0 | -0.65 |
| 0 | 3.79 | 38.62 | 0 | -0.42 |
| 0 | 1.88 | 44.23 | 0 | -0.19 |
| 0 | 0 | 50.03 | 0 | 0 |

The following correction equation can be obtained through data analysis:

$$R_{H2}=T_{H2}-a\times T_{CH4}-b\times T_{CO2}$$

Data in Table 7 are substituted into the equation to conclude that a=0.14097; b=−0.11091.

Therefore, $$R_{H2}=T_{H2}-a\times T_{CH4}-b\times T_{CO2}=T_{H2}-0.14097\times T_{CH4}+0.11091\times T_{CO2}$$

3) Calculate the Calorific Value of Coal Gas

According to the above gas concentration, the calorific value of coal gas is obtained through substituting $T_{CO}$, $T_{CH4}$, $R_{CnHm}$ and $R_{H2}$ into the equation $Q=T_{CO}\times 12.64+R_{H2}\times 18.79+T_{CH4}\times 35.88+R_{CnHm}\times 93.18$, in which, Q is expressed as $MJ/m^3$, 12.64, 18.79, 35.88 and 93.18 are respectively the coefficient of low calorific value of CO, $H_2$, $CH_4$ and $C_nH_m$ expressed as $MJ/m^3$.

This example is provided to design a six-component gas analyzer with the measuring range of CO of 40%, that of $CO_2$ of 20%, that of $CH_4$ of 50%, that of $C_nH_m$ of 10%, that of $H_2$ of 75%, and that of $O_2$ of 25%. This gas analyzer is applicable to many industries, such as coking, biomass pyrolysis, dry distillation, and mixed gas in steel.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for measuring components and calorific value of coal gas, the method comprising:

1) measuring a volume concentration of $H_2$ ($T_{H2}$) in the coal gas using a thermal conductivity detector (TCD), and measuring a volume concentration of $O_2$ in the coal gas using an electrochemical detector (ECD);

2) measuring a volume concentration of CO ($T_{CO}$), a volume concentration of $CO_2$ ($T_{CO2}$), a volume concentration of $CH_4$ ($T_{CH4}$), and a volume concentration of $C_nH_m$ ($T_{CnHm}$) in the coal gas using a non-dispersive infrared (NDIR) technology;

3) calculating a revised volume concentration of $C_nH_m$ ($R_{CnHm}$) using the equation $R_{CnHm}=T_{CnHm}-A\times T_{CH4}$, wherein A is 0.02868, and $T_{CnHm}$ and $T_{CH4}$ are as defined in 2);

4) calculating a revised volume concentration of $H_2$ ($R_{H2}$) using the equation $R_{H2}=T_{H2}-a\times(T_{CH4}+R_{CnHm})-b\times T_{CO2}$, wherein a is 0.13989, b is −0.11026, $T_{H2}$ is as defined in 1), $T_{CH4}$ and $T_{CO2}$ are as defined in 2), and $R_{CnHm}$ is as defined in 3); and 5) calculating the calorific value of the coal gas (Q) using the equation $Q=T_{CO}\times12.64+R_{H2}\times18.79+T_{CH4}\times35.88+R_{CnHm}\times93.18$, wherein $T_{CO}$ and $T_{CH4}$ are as defined in 2), $R_{H2}$ is as defined in 4), and $R_{CnHm}$ is as defined in 3).

2. The method of claim 1, wherein in the process of measuring the volume concentration of $CH_4$ using the NDIR, a center wavelength (CWL)/half-peak bandwidth (HWBP) of a selected narrowband filter is 7.85±0.05 μm/180±5 nm.

3. The method of claim 1, wherein in the process of measuring the volume concentration of $C_nH_m$ using the NDIR, a CWL/HWBP of a selected narrowband filter is 3.46±0.05 μm/120±5 nm.

4. The method of claim 1, wherein in the process of measuring the volume concentration of CO using the NDIR, a CWL/HWBP of a selected narrowband filter is 4.66±0.05 μm/90±5 nm.

5. The method of claim 1, wherein in the process of measuring the volume concentration of $CO_2$ using the NDIR, a CWL/HWBP of a selected narrowband filter is 4.26±0.05 μm/120±5 nm.

6. A method for measuring components and calorific value of coal gas, the method comprising:

1) measuring a volume concentration of $H_2$ ($T_{H2}$) in the coal gas using a thermal conductivity detector (TCD), and measuring a volume concentration of $O_2$ in the coal gas using an electrochemical detector (ECD);

2) measuring a volume concentration of CO ($T_{CO}$), a volume concentration of $CO_2$ ($T_{CO2}$), a volume concentration of $CH_4$ ($T_{CH4}$), and a volume concentration of $C_nH_m$ ($T_{CnHm}$) in the coal gas using a non-dispersive infrared (NDIR) technology;

3) calculating a revised volume concentration of $C_nH_m$ ($R_{CnHm}$) using the equation $R_{CnHm}=T_{CnHm}-A\times T_{CH4}$, wherein A is 0.02837, and $T_{CnHm}$ and $T_{CH4}$ are as defined in 2);

4) calculating a revised volume concentration of $H_2$ ($R_{H2}$) using the equation $R_{H2}=T_{H2}-a\times(T_{CH4}+R_{CnHm})-b\times T_{CO2}$, wherein a is 0.14097, b is −0.11091, $T_{H2}$ is as defined in 1), $T_{CH4}$ and $T_{CO2}$ are as defined in 2), and $R_{CnHm}$ is as defined in 3); and 5) calculating the calorific value of the coal gas (Q) using the equation $Q=T_{CO}\times12.64+R_{H2}\times18.79+T_{CH4}\times35.88+R_{CnHm}\times93.18$, wherein $T_{CO}$ and $T_{CH4}$ are as defined in 2), $R_{H2}$ is as defined in 4), and $R_{CnHm}$ is as defined in 3).

7. The method of claim 6, wherein in the process of measuring the volume concentration of $CH_4$ using the NDIR, a center wavelength (CWL)/half-peak bandwidth (HWBP) of a selected narrowband filter is 7.85±0.05 μm/180±5 nm.

8. The method of claim 6, wherein in the process of measuring the volume concentration of $C_nH_m$ using the NDIR, a CWL/HWBP of a selected narrowband filter is 3.46±0.05 μm/120±5 nm.

9. The method of claim 6, wherein in the process of measuring the volume concentration of CO using the NDIR, a CWL/HWBP of a selected narrowband filter is 4.66+0.05 μm/90±5 nm.

10. The method of claim 6, wherein in the process of measuring the volume concentration of $CO_2$ using the NDIR, a CWL/HWBP of a selected narrowband filter is 4.26±0.05 μm/120±5 nm.

* * * * *